(12) United States Patent
Wang

(10) Patent No.: US 9,623,053 B2
(45) Date of Patent: Apr. 18, 2017

(54) PHARMACEUTICAL COMPOSITION FOR TREATING AIDS AND PREPARATION METHOD THEREOF

(71) Applicant: Zhonglin Wang, Shangqiu (CN)

(72) Inventor: Zhonglin Wang, Shangqiu (CN)

( * ) Notice: Subject to any disclaimer, the term of this patent is extended or adjusted under 35 U.S.C. 154(b) by 0 days.

(21) Appl. No.: 14/438,451

(22) PCT Filed: Dec. 31, 2013

(86) PCT No.: PCT/CN2013/091013
§ 371 (c)(1),
(2) Date: Apr. 24, 2015

(87) PCT Pub. No.: WO2015/100579
PCT Pub. Date: Jul. 9, 2015

(65) Prior Publication Data
US 2016/0030491 A1    Feb. 4, 2016

(51) Int. Cl.
A61K 36/068 (2006.01)
A61K 36/8964 (2006.01)
A61K 35/64 (2015.01)
A61K 36/804 (2006.01)
A61K 9/48 (2006.01)
A61K 36/64 (2006.01)
A61K 36/88 (2006.01)

(52) U.S. Cl.
CPC ............ *A61K 35/64* (2013.01); *A61K 9/48* (2013.01); *A61K 36/068* (2013.01); *A61K 36/64* (2013.01); *A61K 36/804* (2013.01); *A61K 36/88* (2013.01); *A61K 36/8964* (2013.01)

(58) Field of Classification Search
CPC ............ A61K 36/068; A61K 36/8964; A61K 36/804; A61K 35/642
USPC .............. 424/195.15, 208.1, 773, 408, 538
See application file for complete search history.

(56) References Cited

FOREIGN PATENT DOCUMENTS

| CN | 1081895 A | | 2/1994 |
|---|---|---|---|
| CN | 1091953 A | | 9/1994 |
| CN | 1060357 C | * | 1/2001 |
| CN | 1552437 A | | 12/2004 |
| CN | 1736393 A | * | 2/2006 |
| CN | 1736393 A | | 2/2006 |
| CN | 101019861 A | | 8/2007 |
| CN | 101450084 A | | 6/2009 |
| CN | 101683499 A | * | 3/2010 |
| CN | 101785828 A | | 7/2010 |
| CN | 102058764 A | * | 5/2011 |
| CN | 102058764 A | | 5/2011 |

OTHER PUBLICATIONS

Supplemental European Search Report issued in European Patent Application No. 13895447.4 on Nov. 24, 2015.
Fu et al., "Research on the Anti-HIV-1 Active Constituents of Cordyceps Militaris", Acta Scientiarum Naturalium Universitatis Nankaiensis, vol. 40, No. 5 (2007) pp. 91-95.
Fu, "Studies on Prevention and Treatment of AIDS with Traditional Chinese Medicine", Henan Journal of Preventive Medicine, vol. 5, No. 4 (1994) pp. 233-234.
International Search Report and Written Opinion issued in International Application No. PCT/CN2013/091013 on Aug. 13, 2014.
Wei, "The Research Progress on Treating Acquired Immune Deficiency Syndrome with Chinese Herbal Medicine", Harbin Medical Journal, vol. 32, No. 4 (2012) pp. 314-315.

* cited by examiner

*Primary Examiner* — Chris R Tate
*Assistant Examiner* — Deborah Davis
(74) *Attorney, Agent, or Firm* — Birch, Stewart, Kolasch & Birch, LLP

(57) ABSTRACT

The present invention belongs to a pharmaceutical composition preparation field of traditional Chinese medicine, and more particularly relates to a pharmaceutical composition for treating AIDS and preparation method thereof. The pharmaceutical composition of the present invention for treating AIDS comprises the following raw medicinal materials: *Cordyceps Sinensis* in an amount of 3-6 parts by weight, Dried *Radix Rehmanniae* in an amount of 4-12 parts by weight, *Mylabris* in an amount of 1-3 parts by weight, and *Rhizoma Anemarrhenae* in an amount of 3-6 parts by weight. The clinical trials show that the pharmaceutical composition has a relatively good therapeutic effect for treating AIDS.

9 Claims, No Drawings

PHARMACEUTICAL COMPOSITION FOR TREATING AIDS AND PREPARATION METHOD THEREOF

FIELD OF THE INVENTION

The present invention belongs to a pharmaceutical composition preparation field of traditional Chinese medicine, and more particularly relates to a pharmaceutical composition for treating AIDS and preparation method thereof.

BACKGROUND OF THE INVENTION

As is well known, Acquired Immune Deficiency Syndrome (AIDS) is the most serious and stubborn infectious disease all over the world, which was first found in the United States in the 20th century. It has been classified as one of category B fulminating infectious diseases by the World Health Organization (WTO), and its mortality rate ranks seventh among the world's top ten diseases. As a result, AIDS is also known as "Super cancer" by the medical community due to high mortality rate and no cure in Western medicine.

In terms of the pathogenic and pathologic mechanisms of AIDS, Western medicine holds that AIDS is an immunodeficiency disease in which human immunodeficiency virus (HIV) attacks the CD4 cells of T lymphocytes. At last, the body's immune functions fall into disorder due to immunodeficiency, and the resulting opportunistic infections cause the patient's disease and even death. While from the perspective of epidemic febrile disease of Chinese medicine, AIDS is caused by an exogenous pathogenic factor, namely, one of the six pathogenic factors, as a collective term for exogenous pathogenic wind, cold, summer-heat, dampness, dryness, and fire. So by which kind of pathogenic factors people with AIDS are infected and develop the disease? According to numerous clinical symptoms, physical signs, and Chinese medical syndromes of AIDS patients, AIDS is called "epidemic toxin wind", and AIDS patients are exogenously infected with fatal "epidemic toxin wind" and develop the disease, by determination of etiologic factor based on differentiation, on the basis of Chinese medicine theory of treatment based on syndrome differentiation and determination of etiologic factor based on differentiation.

Chinese medicine holds that wind is YANG-pathogen, being characterized by opening-dispersing, easy mobility and changeability, which can coerce all other pathogenic factors into causing diseases. Wind pathogen is usually apt to consume essence and injure fluid, leading to depleted YIN fluid and then disease development, so Chinese medical syndromes of upper hyperactivity of deficient YANG due to depleted YIN fluid are more common; consuming essence and injuring fluid usually start with depleted kidney YIN and liver YIN, meanwhile, of which depleted kidney YIN and liver YIN is the most serious syndrome. In fact, kidney YIN is the genuine YIN, and liver and kidney are homogenous, so the syndromes of depleted kidney YIN and liver YIN induced by depleted YIN fluid account for a majority; moreover, clinical symptoms of AIDS are complex and changeable because of the feature that wind pathogen coerces all other pathogenic factors to cause diseases and is changeable.

In terms of treatment principles and mechanisms of AIDS, Western medicine holds that AIDS is an immunodeficiency disease in which human immunodeficiency virus (HIV) attacks the CD4-positive T lymphocytes. T lymphocyte is a significant component of human peripheral immune system, and human bone marrow is one of the important central immune organs, therefore invasion and injury of HIV in peripheral immune system are also bound to impair and injure the central immune system. Consequently in treatment, we shall not only inhibit, kill and clear viruses, but also adjust and enhance the body immunity to strengthen resistance against diseases, namely a good therapeutic effect can only be achieved after treatment through giving equal importance to the two aspects. This is what we often say that "doing two jobs at once and attaching equal importance to each". On the basis of enhancing the body immunity to strengthen body resistance against diseases, treating with drugs to activate enzymes in human immune system, and under the influence of activated enzymes, bone marrow hematopoietic system, that is, central immune system, enables the genes in immune cells to mutate and recombine, producing cytotoxic T lymphocytes (CTL) with the ability to inhibit, kill and clear CD4 lymphocytes infected with HIV, not only killing and clearing free HIV viruses in the blood, but also killing and clearing CD4 lymphocytes infected with HIV, which is the only way to cure AIDS. So from the perspective of Western medicine, the way of treating AIDS should be starting with bone marrow treatment, which is the way from the root and in the right direction. As it is the prime example of clinical practice that an American, Timothy Ray Brown, has been cured of AIDS using bone marrow transplant.

However, as is well known, there exist some problems in AIDS treatment with Western medicine and Western drugs, and Western drugs are not able to cure AIDS, whether domestic drugs or imported ones, whether first-line drugs or second-line drugs or third-line drugs, whether single medication or combination therapy or cocktail therapy. It can be seen, there inevitably exist some problems and defects in Western medicine and Western drugs. Above all, AIDS was first found in the United States with advanced science, and was proven to be caused by HIV infection in human body after experimental research. Using quite advanced scientific experiments, western countries found and interpreted the pathological mechanism that HIV infection causes AIDS, which is very correct. At the same time in treatment, it is a normal therapeutic approach to inhibit, kill and clear HIV viruses using antiviral drugs. HIV invades the human body's immune system in view of its own characteristics, which makes the antiviral drugs meet with many difficulties in treating the disease, and almost a formidable obstacle.

First of all, HIV virus exists in two forms after it invades the human body: one is the form of free virus, and the other is integrated into the genes of invaded CD4 lymphocytes. Western antiviral drugs in development only have effects on free viruses, whereas don't do much for the viruses that have already invaded into the genes of CD4 lymphocytes, which allows the HIV viruses in the genes of CD4 lymphocytes to still replicate, and not to be killed and cleared. HIV viruses inside replicate and multiply to large numbers, and cause the opportunistic infections resulting in the patient's death, especially in a state when the body immunity is gradually decreasing. Secondly, Western antiviral drugs work by the mechanism of inhibiting HIV reverse transcriptase activity (HIV virus is a type of retrovirus). Therefore when treating AIDS using Western antiviral drugs, they inhibits the enzyme activity in the body's normal cells while inhibiting HIV reverse transcriptase activity, in particular, the inhibition on the enzyme activity in the lymphatic system can inhibit and disturb the function of lymphatic system (namely the immune system). At the same time, enzymes of liver function and bone marrow hematopoietic system would be greatly inhibited and disturbed, which is one of the reasons why there are plenty of side effects in Western antiviral drugs. Thus, neither do the common Western drugs have the ability to inhibit, kill and clear HIV viruses and CD4 lymphocytes infected with HIV, nor simultaneously do they have the ability to enhance the body immunity to strengthen resistance against diseases. Even if combining usage of multiple antiviral drugs, also known as cocktail therapy, it can just properly control the virus variation, suppress the virus replication to the maximum extent, and prevent drug resistance of the virus. Obviously, it is the basic reason why Western antiviral drugs are not able to cure AIDS, which renders the worldwide problem AIDS still unable to be solved for a long time.

SUMMARY OF THE INVENTION

For this purpose, in the present invention, the technical problem to be solved is to provide a pharmaceutical composition for treating AIDS, and further provide a preparation method thereof.

The pharmaceutical composition for treating AIDS, wherein the composition comprises the following raw medicinal materials:
  *Cordyceps Sinensis* in an amount of 3-6 parts by weight,
  Dried *Radix Rehmanniae* in an amount of 4-12 parts by weight,
  *Mylabris* in an amount of 1-3 parts by weight, and
  *Rhizoma Anemarrhenae* in an amount of 3-6 parts by weight.

Preferably, the composition comprises the following raw medicinal materials:
  *Cordyceps Sinensis* in an amount of 4 parts by weight,
  Dried *Radix Rehmanniae* in an amount of 9 parts by weight,
  *Mylabris* in an amount of 2 parts by weight, and
  *Rhizoma Anemarrhenae* in an amount of 4 parts by weight.
or
  *Cordyceps Sinensis* in an amount of 5 parts by weight,
  Dried *Radix Rehmanniae* in an amount of 11 parts by weight,
  *Mylabris* in an amount of 1 parts by weight, and
  *Rhizoma Anemarrhenae* in an amount of 5 parts by weight
or
  *Cordyceps Sinensis* in an amount of 6 parts by weight,
  Dried *Radix Rehmanniae* in an amount of 7 parts by weight,
  *Mylabris* in an amount of 1.5 parts by weight, and
  *Rhizoma Anemarrhenae* in an amount of 4.2 parts by weight.

The pharmaceutical composition is made into clinically acceptable dosage forms, including powders, granules, tablets, capsules, pills, sustained release preparations and oral liquid preparations, according to the conventional technologies after being added with conventional excipients.

The present invention also discloses a method for preparing the pharmaceutical composition, comprising weighing out each of the raw medicinal materials according to predetermined parts by weight, adding conventional excipients into the raw materials to form a mixture, and making the mixture into clinically acceptable dosage forms, including powders, granules, tablets, capsules, pills, sustained release preparations and oral liquid preparations, according to the conventional technologies.

The conventional technology can refer to water extraction, for example, adding conventional volume of water into the mixture and decocting it two or three times to produce aqueous solutions, merging the aqueous solutions, then concentrating and drying the merged solution using ethanol to produce a dried extract, and making the dried extract into a number of different dosage forms according to the conventional technologies. The mixture can also be extracted, purified, and vacuum dried according to other conventional methods, then made into a number of different dosage forms.

The method also includes steps of impurity elimination and selection of the raw medicinal materials, moreover, the *Mylabris* in the form of Chinese herbal slices, or otherwise known as "toxic" raw medicinal materials, undergoes processing according to the traditional Master Lei's processing method to attenuate toxicity and enhance efficacy. The Master Lei's processing method for processing the *Mylabris* can be one of those conventional methods described in "Explanation on Master Lei's Properties of Drugs Processing" in the prior art.

The present invention further discloses a use of the pharmaceutical composition in preparing medicine for treating AIDS.

From the perspective of epidemic febrile disease of Chinese medicine, AIDS should be called "epidemic toxin wind" in Chinese medicine. The pathogen of "epidemic toxin wind" invades liver and kidney of lower warmer in human body and causes the disease. Wind is YANG-pathogen, which is characterized by opening-dispersing, easy mobility and changeability, and is usually apt to consume essence and injure fluid, leading to pathological changes in human body. Chinese medicine theories hold that kidney governs bones to produce marrow, governs growth and development, and is the congenital foundation of human body. Moreover, liver and kidney are homogenous, kidney YIN is the genuine YIN in human body, so the pathogen of "epidemic toxin wind" is apt to hurt YIN in liver and kidney of lower warmer to cause disease development. Consequently in treatment, the fundamental way to treat AIDS is to nourish the YIN in liver and kidney and purge the pathogen of "epidemic toxin wind", which is so-called "counteract one toxin with another" to drive the pathogenic factors to go out.

The pharmaceutical composition of the present invention complies with theoretical thoughts and methods of "discussing diseases based on bones and treating diseases based on bones", and is developed from large numbers of Chinese herbal recipes for treating osteomyelitis, osteocarcinoma and myelomatosis; it has the power of penetrating muscles and bones, runs through all channels and goes anywhere in the body, and is adept at entering into the blood, goes straight into liver and kidney of lower warmer, purges fire to consolidate YIN, enriches the essence to benefit the marrow, reinforces the prenatal base of kidney, clears away heat and toxic materials, soothes the liver and regulates Qi, purges fire from liver and gallbladder, removes the wind pathogen to guard against the pathogenic factors, also called "counteract one toxin with another", drives the pathogenic factors to go out, pushes the medicine to the location of disease, drives out the pathogenic factors to stabilize the body, is adept at purging toxins out of the body to make the pathogenic factors disappear and not to keep them inside, exerts tonification and purgation in combination to make the pathogenic factors have no place to shelter themselves.

The pharmaceutical composition of the present invention has effects of anti-bacterium, anti-inflammation, anti-virus, anti-allergy, and anti-hypersensitivity, and plays bidirectional roles of "strengthening the body resistance to eliminate pathogenic factors" and "eliminating pathogenic factors not to harm the body resistance", thereby can be effective in treating AIDS.

TEST EXAMPLE

Test Example 1

Clinical Report on Treatment of One AIDS Patient Using the Pharmaceutical Composition of the Present Invention 1. General information of the patient in attempt to receive treatment:
Gender, Male;
Age, 34 years old;
Domicile of origin, Suqian, Jiangsu Province;
Route of infection, Body fluid transmission;
Estimated infection time, 2-3 years ago;
2. Method of Administration and Dosage:

He began to receive treatment using the medicine of the present invention on Oct. 11, 2011, and the medicine was withdrawn on Oct. 21, 2012, which means the treatment ended. The treatment lasted for one year and ten days.

During the treatment course, the capsule preparation prepared in Embodiment 1 was used for treatment. In the beginning, 6-7 capsules each time, and three times a day. 10 days later the dosage raised to 8-10 capsules each time, three times a day, and the maximum dosage was not more than 13 capsules each time, three times a day. The medicine administration amount varies and depends on the severity level of the patient's disease, different body constitutions, and different reactions to the medicine.

In the course of administration, the adjustment criteria for medicine amount are based on monitoring stool forms. The optimal administration amount of medication in a patient is determined by his/her loose and watery stools after medicine administration. When the stool becomes dry and hard, the amount needs to be raised, adding one capsule each time for adjustment until the stool appears loose and watery; whereas when the stool becomes too watery, the amount needs to be decreased, reducing one capsule each time for adjustment until the stool appears loose and watery.

In the course of administration, avoid eating green beans and products made from green bean, Panax ginseng, Korean ginseng, American ginseng and other ginseng tonics, keep off sour, spicy, raw, cold food or cool beer, etc. Take the medicine before or after meals, and drink more plain boiled water.

3. International criteria for functional AIDS cure:

In 2011, World Health Organization (WHO) proposed a plan for treating AIDS, called "Towards an HIV cure". The goal of the plan is as follows: the AIDS patient's immune system is able to completely control viral rebound, no need to perform antiviral treatment, although there still exists HIV genetic material in the body after treatment with effective drugs.

The criteria described above include the following contents:

(1) the clinical symptoms disappear or almost disappear after treatment;

(2) several parameters determined by immunocytology reach or approach the levels in normal people, that is, the counts of CD4, CD8, CD3 and ratios between them reach or approach the levels in normal people; and (3) the viral load reaches the international criteria, that is, lower than 50 copies/ml.

4. Treatment Results

Before treatment, the CD4 count was 402, CD8 count was 1012, CD4/CD8 ratio was 0.39, and the viral load was 77000 copies/ml; he had symptoms of night sweats, anorexia, and emaciation before treatment. 6 months after treatment, the CD4 count was 507, CD8 count was 1150, CD4/CD8 ratio was 0.44, and the viral load was 38000 copies/ml; his clinical symptoms almost disappeared, appetite was increased, and his weight gained by 4 kg.

After the treatment ended, the test results on Nov. 24, 2013 showed that: the CD4 count was 334, CD8 count was 635, CD4/CD8 ratio was 0.54, and the viral load was 7769 copies/ml, his clinical symptoms completely disappeared, weight gained by 8 kg, which reached the level of initial cure. During the treatment course, the patient did not take any other medicines except the medicine of the present invention, which was characterized by continuous administration without interruption. Place of detection was at Beijing You An Hospital, Capital Medical University.

The patient's health status continued to be monitored after medicine withdrawal, and the patient did not take any other commonly used medicines for treatment, under those circumstances, it was found that the patient's immunocytology parameters (namely determination of CD4, CD8, and so on) gradually reached or approached the levels in normal people under the influence of medicine, and the viral load continued to show a trend of descent again, even more close to the normal levels, moreover the original symptoms did not recur.

Consequently, for this patient who was transmitted through bodily fluids, after treatment with the medicine of the present invention for more than one year, completely without using antiviral drugs or other drugs, not only did the viral load drop obviously, without rebound, but also the results of immunocytology determination showed that the patient's immune system was adjusted, reconstructed and improved during the course of treatment with the medicine of the present invention which is a pure Chinese medicine preparation, CD8 count dropped gradually, and CD4/CD8 ratio rose gradually. Furthermore, the viral load would continue to drop constantly, without rebound, on the basis of immune system reconstruction. Even in a longer period after medicine withdrawal, the viral load would eventually drop to below the lower detection limit (LDL) under the influence of his own immune system, until reach or approach the levels in normal people, accomplishing a goal of complete cure.

More importantly, the reconstructed and improved immune system can still maintain certain self-healing effects even after medicine withdrawal, and the parameters in all aspects still remain the relatively stable levels as in normal people, showing that therapeutic effects of the pharmaceutical composition are reliable and stable in enhancing the patient's body immunity to strengthen resistance against diseases. Under the influence of the pharmaceutical composition, the impaired immune system of the patient would recover in case after being adjusted, reconstructed and improved, and the immune system would remain quite stable and durable after recovery, which can reach the immunity level as in normal people. Moreover, the body immunity that has recovered to the normal state would still be provided with the ability to inhibit, kill and clear HIV viruses.

Test Example 2

Clinical Report on Treatment of 30 AIDS Patients Using the Pharmaceutical Composition of the Present Invention For the 30 patients in attempt to receive treatment, capsule preparation made from the pharmaceutical composition in the embodiments described below was used for treatment. The study population was half men and half women, age ranged from 30 to 60 years old, the administration period lasted for one year, and the administration dosages and precautions were the same as described in Test Example 1. During the course of administration, the patients did not take any antiviral drugs or other drugs for treating AIDS, and the administration period lasted for one consecutive year.

Before taking medicine for treatment, all the patients had varying degrees of symptoms of diarrhea, general weakness, and skin pruritus, caught colds frequently that were not easy to recover, and accompanied by a condition of significant weight loss. Among all the 30 patients, the average absolute value of CD4 count was about 200, the average viral load was up to 70000 copies/ml, and HIV antibody tests showed positive results.

Before taking medicine of the present invention, the features of CD4 cell were detected among all the patients, and during the treatment course of one year, the features of CD4 cell and viral load were detected every three months with those before treatment as control, in order to monitor the therapeutic effects.

At three months after treatment, the features of CD4 cell and viral load were detected among all the 30 patients, and the results showed that the levels of CD4 cell in all the patients were increased in varying degrees, with an average increase amplitude reaching 60%, in other words, the patients' immunities were enhanced in varying degrees, and the levels of CD4 cell in 26 of these patients reached the normal degree. The above results also indicated that the increase amplitude was inversely proportional to the patients' age, the patient who achieved the highest increase amplitude was 32 years old, with the increase amplitude of CD4 cell level up to 200%, and the patient who achieved the lowest increase amplitude was 60 years old, with the increase amplitude being about 15%. The viral load in all patients dropped in varying degrees, with the average viral load reaching below 45000 copies/ml. Thus it can be seen that the medicine of the present invention takes effect in a shorter time, with a more rapid onset of action.

At seven months after treatment, the features of CD4 cell and viral load were detected a second time among all the 30 patients, and the results showed that the levels of CD4 cell in half of the patients dropped slightly compared with those at three months after treatment, but still obviously higher than those before treatment; for the other half of the patients, the levels of CD4 cell were increased constantly, but the increase amplitude became not obvious; the average value of CD4 cell level among all the 30 patients was equivalent to that detected at three months after treatment. The viral load in all patients dropped again with a minor amplitude, and the average value was lower than 20000 copies/ml. Thus it can be seen that, after seven months of treatment, the patients' immunities had tended to stabilize although occasional fluctuations were observed, so the medicine was basically effective in enhancing the immunity.

After the one-year treatment ended, the features of CD4 cell were detected a third time among all the 30 patients, and the results showed that the levels of CD4 cell in more than half of the patients dropped compared with those at seven months after treatment, but still obviously higher than those before treatment; for the other nearly half of the patients, the levels of CD4 cell were increased constantly, but the increase amplitude became lower. For all the 30 patients, the average value of CD4 cell level was increased compared with that detected at the beginning of treatment. The levels of CD4 cell in all patients were increased in varying amplitude, with the average increase amplitude reaching nearly 50%, in 25 of these patients the levels of CD4 cell reached the normal degree, and the clinical symptoms almost disappeared. The viral load in all patients dropped constantly, with the average level lower than 8000 copies/ml.

Thus it can be seen that, after one year of treatment, the patients' immunities had tended to stabilize, the clinical symptoms before treatment were relieved in varying amplitude, even disappeared, and the weights in all patients also gained in varying amplitude. Moreover, no side effects of medicine administration were observed in all the 30 patients, and at the time of medicine withdrawal, the clinical manifestations in all patients performed well, and the original clinical symptoms completely disappeared.

Consequently, the medicine of the present invention is able to effectively enhance the patients' immunities, and has a relatively good therapeutic effect against AIDS.

One and a half years after the medicine withdrawal, the status of the patients after medicine withdrawal was continued to be followed-up and monitored. During the course of drug withdrawal, 10 of these patients took other therapeutic drugs, and the remaining patients did not take other drugs. During the course of drug withdrawal, 18 of these patients responded well, the original clinical symptoms were not observed to recur and completely disappeared; 3 patients died of deep infections; another 9 patients showed various other uncomfortable symptoms, including abdominal pains, nausea, being liable to catch cold and so on, but the symptoms were relatively stable, and the original clinical symptoms were not observed to recur. Through determination of the levels in the patients' viral load, it is found that the levels in each patient's viral load still continued to drop in varying degrees, even under the circumstances of medicine withdrawal, thus from the therapeutic perspective of a patient's own immune system reconstruction, the medicine of the present invention is still able to achieve the constant treatment goal, even after the medicine withdrawal.

Two and a half years after the medicine withdrawal, the status of the 27 patients alive was continued to be followed-up and monitored. During that course, another 4 patients took other anti-AIDS drugs, and another 2 patients stopped taking other therapeutic drugs; during that course, one additional patient died; other patients' overall survival status was in good condition, and the clinical symptoms completely disappeared, although occasional discomfort emerged. More importantly, the level of viral load in each patient alive still showed a constantly dropping status, and gradually approached the degree of "functional cure" in clinical practice.

DETAILED DESCRIPTION OF THE EMBODIMENTS

Embodiment 1

Capsules 4 kg of *Cordyceps Sinensis*, 9 kg of Dried *Radix Rehmanniae*, 2 kg of *Mylabris*, and 4 kg of *Rhizoma Anemarrhenae*.

*Mylabris* of predetermined weight was taken and subjected to processing according to the documented Master Lei's processing method to attenuate toxicity and enhance efficacy;

The *Cordyceps Sinensis*, Dried *Radix Rehmanniae*, and *Rhizoma Anemarrhenae* of predetermined weights were taken, and subjected to impurity elimination and selection of high quality medicinal materials, then were crushed and mixed (or mixed followed by being crushed) to produce a mixture. Adding conventional volume of water into the mixture and decocting and extracting it twice, followed by drying to produce an extractum. Then the extractum was made into the dosage form of capsules according to conventional technologies after being added with conventional excipients.

Embodiment 2

Tablets 5 kg of *Cordyceps Sinensis*, 11 kg of Dried *Radix Rehmanniae*, 1 kg of *Mylabris*, and 5 kg of *Rhizoma Anemarrhenae*.

*Mylabris* of predetermined weight was taken and subjected to processing according to the documented Master Lei's processing method to attenuate toxicity and enhance efficacy;

The *Cordyceps Sinensis*, Dried *Radix Rehmanniae*, and *Rhizoma Anemarrhenae* of predetermined weights were taken, and subjected to impurity elimination and high quality materials selection, then were crushed and mixed (or mixed followed by being crushed) to produce a mixture. The mixture was made into the dosage form of tablets according to conventional technologies after being added with conventional excipients.

Embodiment 3

Pills 6 kg of *Cordyceps Sinensis*, 7 kg of Dried *Radix Rehmanniae*, 1.5 kg of *Mylabris*, and 4.2 kg of *Rhizoma Anemarrhenae*.

*Mylabris* of predetermined weight was taken and subjected to processing according to the documented Master Lei's processing method to attenuate toxicity and enhance efficacy;

The *Cordyceps Sinensis*, Dried *Radix Rehmanniae*, and *Rhizoma Anemarrhenae* of predetermined weights were taken, and subjected to impurity elimination and high quality materials selection, then were crushed and mixed (or mixed followed by being crushed) to produce a mixture. The mixture was made into the dosage form of pills according to conventional technologies after being added with conventional excipients.

Embodiment 4

Granules 3 kg of *Cordyceps Sinensis*, 12 kg of Dried *Radix Rehmanniae*, 1 kg of *Mylabris*, and 6 kg of *Rhizoma Anemarrhenae*.

The above raw medicinal materials were taken, and were made into the dosage form of granules according to conventional technologies after being added with conventional excipients.

Embodiment 5

Capsules 6 kg of *Cordyceps Sinensis*, 4 kg of Dried *Radix Rehmanniae*, 3 kg of *Mylabris*, and 3 kg of *Rhizoma Anemarrhenae*.

*Mylabris* of predetermined weight was taken and subjected to processing according to the documented Master Lei's processing method to attenuate toxicity and enhance efficacy;

The *Cordyceps Sinensis*, Dried *Radix Rehmanniae*, and *Rhizoma Anemarrhenae* of predetermined weights were taken, and subjected to impurity elimination and high quality materials selection, then were crushed and mixed (or mixed followed by being crushed) to produce a mixture. The mixture was made into the dosage form of capsules according to the conventional technologies after being added with conventional excipients.

Obviously, the above embodiments are for purpose of clear illustration and are not intended to limit the embodiment mode. It will be obvious to those skilled in the art that changes and modifications may be made without departing from the invention in its broader aspects, and, therefore, the aim of the appended claims is to cover all such changes and modifications as fall within the true spirit and scope of the invention.

The invention claimed is:

1. A pharmaceutical composition for treating AIDS, wherein the composition comprises the following raw medicinal materials:
   *Cordyceps Sinensis* in an amount of 3-6 parts by weight,
   Dried *Radix Rehmanniae* in an amount of 4-12 parts by weight,
   *Mylabris* in an amount of 1-3 parts by weight, and
   *Rhizoma Anemarrhenae* in an amount of 3-6 parts by weight.

2. The pharmaceutical composition according to claim 1, wherein the composition comprises the following raw medicinal materials:
   *Cordyceps Sinensis* in an amount of 4 parts by weight,
   Dried *Radix Rehmanniae* in an amount of 9 parts by weight,
   *Mylabris* in an amount of 2 parts by weight, and
   *Rhizoma Anemarrhenae* in an amount of 4 parts by weight.

3. The pharmaceutical composition according to claim 1, wherein the composition comprises the following raw medicinal materials:
   *Cordyceps Sinensis* in an amount of 5 parts by weight,
   Dried *Radix Rehmanniae* in an amount of 11 parts by weight,
   *Mylabris* in an amount of 1 parts by weight, and
   *Rhizoma Anemarrhenae* in an amount of 5 parts by weight.

4. The pharmaceutical composition according to claim 1, wherein the composition comprises the following raw medicinal materials:
   *Cordyceps Sinensis* in an amount of 6 parts by weight,
   Dried *Radix Rehmanniae* in an amount of 7 parts by weight,
   *Mylabris* in an amount of 1.5 parts by weight, and
   *Rhizoma Anemarrhenae* in an amount of 4.2 parts by weight.

5. The pharmaceutical composition according to claim 1, wherein the pharmaceutical composition is made into clinically acceptable dosage forms selected from the group consisting of powders, granules, tablets, capsules, pills, sustained release preparations and oral liquid preparations.

6. The pharmaceutical composition according to claim 2, wherein the pharmaceutical composition is made into clinically acceptable dosage forms selected from the group consisting of powders, granules, tablets, capsules, pills, sustained release preparations and oral liquid preparations.

7. The pharmaceutical composition according to claim 3, wherein the pharmaceutical composition is made into clinically acceptable dosage forms selected from the group consisting of powders, granules, tablets, capsules, pills, sustained release preparations and oral liquid preparations.

8. The pharmaceutical composition according to claim 4, wherein the pharmaceutical composition is made into clinically acceptable dosage forms selected from the group consisting of powders, granules, tablets, capsules, pills, sustained release preparations and oral liquid preparations.

9. A pharmaceutical composition for treating AIDS, wherein the anti-viral agents of the composition consists of the following raw medicinal materials:
  *Cordyceps Sinensis* in an amount of 3-6 parts by weight,
  Dried *Radix Rehmanniae* in an amount of 4-12 parts by weight,
  *Mylabris* in an amount of 1-3 parts by weight, and
  *Rhizoma Anemarrhenae* in an amount of 3-6 parts by weight.

* * * * *